United States Patent [19]

Reece et al.

[11] 3,960,881

[45] June 1, 1976

[54] METHOD FOR PREPARING 4-CARBOXYTHIAZOLIDINE-2-THIONE

[75] Inventors: Jack E. Reece, Willernie, Minn.; George B. Fozzard, Bartlesville, Okla.

[73] Assignee: Phillips Petroleum Company, Bartlesville, Okla.

[22] Filed: Feb. 12, 1974

[21] Appl. No.: 441,834

Related U.S. Application Data

[60] Continuation-in-part of Ser. No. 246,588, April 24, 1972, abandoned, which is a division of Ser. No. 82,175, Oct. 19, 1970, Pat. No. 3,697,516.

[52] U.S. Cl. .................... 260/306.7 C; 260/243 R; 424/246; 424/270
[51] Int. Cl.$^2$ ........................................ C07D 277/16
[58] Field of Search ........................... 260/306.7 C

[56] References Cited

OTHER PUBLICATIONS

Cook et al., *J. Chem. Soc.*, 1949, 2367–2370.
Elderfield (ed.), *Heterocyclic Compounds*, vol. 5, N.Y. Wiley, 1957, pp. 692–697.
Lukens et al., *Chem. Abstracts*, 52:14065e (1958).
Elderfield (ed.), *Heterocyclic Compounds*, vol. 5, N.Y. Wiley, 1957, p. 679.

*Primary Examiner*—R. Gallagher

[57] ABSTRACT

Certain thiazolidine- and thiazine-2-thione compounds, including 4-carboxythiazolidine-2-thione and 3,4-tetramethylene-4H,5,6-dihydro-1,3-thiazine-2-thione, and methods for preparing same are disclosed.

4 Claims, No Drawings

METHOD FOR PREPARING 4-CARBOXYTHIAZOLIDINE-2-THIONE

This application is a continuation-in-part application of copending application having Ser. No. 246,588, filed Apr. 24, 1972, now abandoned, which in turn is a division of application Ser. No. 82,175, filed Oct. 19, 1970, now U.S. Pat. No. 3,697,516.

This invention relates to the thiazolidine- and thiazine-2-thione compounds characterized by the structural formulas

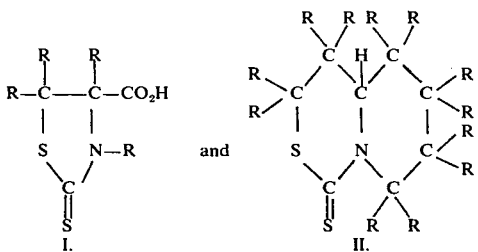

wherein each R is hydrogen or lower alkyl group, e.g., containing from 1 to 6, preferably 1 to 4, carbon atoms, and the total number of carbon atoms in said R substituents is not more than 12, preferably not more than 10; and methods for preparing same.

The compounds characterized by Formula I in the preceding paragraph, and methods for preparing same, are being claimed in this application. The compounds characterized by Formula II in the preceding paragraph, and methods for preparing same, are being claimed in said application, now U.S. Pat. No. 3,697,516.

Examples of compounds of the invention within the scope of the above formulas I and II include, among others, the following: 4-carboxythiazolidine-2-thione; 4-carboxy-5-methylthiazolidine-2-thione; 4-carboxy-5,5-dimethylthiazolidine-2-thione; 4-carboxy-5-ethylthiazolidine-2-thione; 4-carboxy-5-hexylthiazolidine-2-thione; 4-carboxy-5-methyl-5-propylthiazolidine-2-thione; 4-carboxy-5-sec-butylthiazolidine-2-thione; 4-carboxy-4-butyl-5,5-dibutylthiazolidine-2-thione; 3,4-tetramethylene-4H,5,6-dihydro-1,3-thiazine-2-thione; 3,4-tetramethylene-4H,5-methyl-5,6-dihydro-1,3-thiazine-2-thione; 3,4-(3-hexyl)-tetramethylene-4H,5,6-dihydro-1,3-thiazine-2-thione; 3,4-(3-butyl)tetramethylene-4H,5-ethyl-5,6-dihydro-1,3-thiazine-2-thione; 3,4-(3-hexyl)tetramethylene-4H,5-(sec-butyl)-5,6-dihydro-1,3-thiazine-2-thione; 3,4-(3-pentyl-4-ethyl)-tetramethylene-4H,5-pentyl-5,6-dihydro-1,3-thiazine-2-thione; and the like.

The compounds of the invention can be prepared by various methods.

One presently preferred method for preparing the compounds represented by the above Formula I comprises reacting an alkali metal hydroxide, an appropriate aminomercaptan, and carbon disulfide. The alkali metal hydroxide can be any of the hydroxides of sodium, potassium, rubidium, cesium, and lithium, or mixtures thereof. However, for reasons of cost and availability, sodium and/or potassium hydroxide are preferred. The aminomercaptan can be any suitable aminomercaptan capable of reacting with an alkali metal hydroxide and carbon disulfide to give a product within the scope of said Formula I. For example, cysteine hydrochloride hydrate will react with sodium or potassium hydroxide and carbon disulfide to yield 4-carboxythiazolidine-2-thione in accordance with the reaction

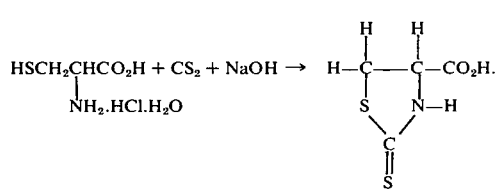

Thus, an appropriate aminomercaptan is one in which the amino group (primary or secondary) and the mercaptan group are on adjacent carbon atoms. Furthermore, as shown by the example, the appropriate mercaptan is an α-amino (or alkylamino)-β-mercaptocarboxylic acid and these compounds can contain from 3 to 15 carbon atoms per molecule to give a product within the scope of Formula I.

The reaction of alkali metal hydroxide, aminomercaptan, and carbon disulfide is preferably carried out in an aqueous reaction admixture of the reactants. Any suitable mol ratio of said reactants can be utilized. Preferably, a mol ratio of alkali metal hydroxide to aminomercaptan within the range of from 10 to 2, more preferably 5 to 3, can be utilized. Preferably, a mol ratio of carbon disulfide to aminomercaptan within the range of 10 to 1, more preferably 2 to 1.2, can be utilized. The reaction temperature is not critical. The reaction(s) take place readily at ambient temperatures, e.g., 60° to 110°F. However, it is within the scope of the invention to employ reaction temperatures outside said range. The reaction(s) is usually carried out at atmospheric pressure, but the use of subatmospheric or superatmospheric pressures is within the scope of the invention. The reaction(s) is preferably carried out with stirring of the reaction admixture for any suitable reaction period, e.g., from 4 to 48, preferably 8 to 30, hours. However, reaction periods outside said ranges can be employed.

One presently preferred method for preparing the compounds represented by the above Formula II comprises acidifying an appropriate (hydroxyalkyl)-piperidine with HCl, preferably gaseous, so as to obtain the corresponding (hydroxyalkyl)piperidine hydrochloride. The acidification is preferably carried out in the presence of an inert solvent. Any suitable solvent which is a solvent for the reactants and which is inert with respect to the reactants and the reaction products can be used in the practice of the invention. Examples of solvents that can be used include the organic solvents such as benzene, toluene, the xylenes, cyclohexane, and the like. The (hydroxyalkyl)piperidine hydrochloride is reacted with a halogen-substitution agent, preferably an agent wherein the halogen is chlorine or bromine, and which is capable of converting said hydroxyalkyl substituent to the corresponding haloalkyl substituent. The resulting (haloalkyl)piperidine hydrochloride is then recovered from the reaction mixture. The recovered (haloalkyl)piperidine hydrochloride is then reacted with an alkali metal hydroxide and carbon disulfide, preferably in an aqueous reaction medium. The alkali metal hydroxide can be any of the hydroxides of sodium, potassium, rubidium, cesium, and lithium, or mixtures thereof. However, for reasons of cost and availability, sodium and/or potassium hydroxides are preferred. The (hydroxyalkyl)piperidine hydrochloride can be any suitable compound capable of undergoing halogen-substitution to give the corresponding (haloalkyl)piperidine hydrochloride. The halogen-substitution agent can be any suitable halogen-substitution agent such as thionyl chloride, phosphorus pentachloride, and the like, which is capable of reacting as described. For example, the (hydroxyalkyl)piperidine hydrochloride can be 2-(2-hydroxyethyl)piperidine which will react with, for example, thionyl chloride to give 2-(2-chloroethyl)piperidine hydrochloride. The (haloalkyl)-piperidine hydrochloride will react with an alkali metal hydroxide and carbon disulfide to yield 3,4-tetramethylene-4H,5,6-dihydro-1,3-thiazine-2-thione. The acidification is preferably carried out at ambient temperatures, e.g., 60° to 110°F, but temperatures outside this range can be used. The reaction of the halogen-substitution agent with the (hydroxyalkyl)piperidine to convert the hydroxyalkyl substituent to the corresponding haloalkyl substituent can be conveiently carried out at the normal refluxing temperature of the reaction mixture. After cooling the reaction mixture, volatile materials are preferably removed at a reduced pressure. The resulting solid residue is then preferably dissolved in water and then reacted with the carbon disulfide and alkali metal hydroxide. Temperature is not critical in this reaction. The reaction can be carried out at ambient temperatures but is preferably carried out at the normal refluxing temperatures of the reaction mixture. The reaction mixture is then acidified, for example, with aqueous HCl, and volatile materials removed at reduced pressure. The remaining product can be purified and crystallized in known manner, e.g., dissolving in an alcohol and recrystallizing. Any suitable mol ratio of the reactants can be utilized. Preferably, a mol ratio of halogen-substituted agent to piperidine hydrochloride will be within the range of from 4 to 1.2, more preferably 2 to 1.4. Preferably, the mol ratio of the alkali metal hydroxide to the (haloalkyl)piperidine hydrochloride will be within the range of from 5 to 1.6, more preferably 2.5 to 1.7. Preferably, the mol ratio of the carbon disulfide to the (haloalkyl)piperidine hydrochloride will be within the range of from 4.0 to 1.2, more preferably 2 to 1.4. All of the reactions are preferably carried out with stirring of the reaction mixture and for any suitable reaction period. For example, the reaction period for the chlorine-substitution reaction can be within the range of from 1 to 4, preferably 1.5 to 3 hours, and the reaction period for the reaction of the carbon disulfide and alkali metal hydroxide with the (haloalkyl)piperidine hydrochloride can be in the range of from 3 to 12, preferably 4 to 8 hours. However, reaction periods outside these ranges can be employed.

The examples given hereinafter will serve to further illustrate the invention. Examples I and II illustrate the preparation of compounds of the invention. Reactants used in preparing the compounds of the invention are known available materials or can be readily prepared by methods known in the art for preparing such materials. Examples III and IV show that compounds of the invention are useful as analgesics. Said compounds are generally administered to mammalian patients in dosages of from 1 to 100 mg/kg of body weight daily, either in single or divided doses over a period of 24 hours. While the compound is active by various routes, oral administration is usually preferred.

The compound can be formulated into various pharmaceutical dosage forms such as tablets, capsules, pills, and the like for immediate or sustained release, by combining it with a suitable pharmaceutically acceptable carrier or diluent according to methods well known in the art. Such dosage forms may additionally include excipients, binders, fillers, flavoring and sweetening agents and other therapeutically inert ingredients necessary in the formulation of the desired pharmaceutical preparation.

EXAMPLE I

Preparation of 4-Carboxythiazolidine-2-thione

Sodium hydroxide (40 g, 1.0 mol), cysteine hydrochloride hydrate (50 g, 0.285 mol) and carbon disulfide (30 g, 0.4 mol) were added in that order to 200 ml water at room temperature. This mixture was stirred for 24 hours. At the end of this period, the reaction mixture was acidified to pH 6 with hydrochloric acid and evaporated to yield a yellow foam. Trituration of this foam with concentrated hydrochloric acid caused crystallization to occur. The white solid thus obtained was recrystallized from 6 N hydrochloric acid to yield 12.2 g (21.2%) of 4-carboxythiazolidine-2-thione, m.p. 183°–184°C with decomposition.

Anal. Calcd. for $C_4H_5O_2NS_2$: C, 29.5; H, 3.1; N, 8.6; S, 39.3. Found: C, 29.6; H, 3.2; N, 8.7; S, 39.5

EXAMPLE II

Preparation of 3,4-Tetramethylene-4H,5,6-dihydro-1,3-thiazine-2-thione 2-(2-Hydroxyethyl)piperidine (100 g, 0.775 mol) was dissolved in benzene and acidified by the introduction of excess gaseous HCl. Thionyl chloride (150 g, 1.25 mol) was then added slowly and this mixture was stirred at gentle reflux for 2 hours. After cooling, volatiles were removed at reduced pressure. The resulting solid residue was dissolved in approximately 200 ml water and transferred to another reaction flask. Carbon disulfide (100 g, 1.25 mol) was added and the resulting combination stirred vigorously as sodium hydroxide (50 g, 1.50 mol, dissolved in 300 ml water) was added. This mixture was stirred at gentle reflux for 6 hours. The mixture was then acidified with 6 N HCl and volatiles were removed at reduced pressure. The solid residue resulting was dissolved in boiling isopropyl alcohol and filtered free of insolubles. The crude product which crystallized from this filtrate was then recrystallized once from aqueous ethanol and once from absolute ethanol to isolate 31 g of 3,4-tetramethylene-4H,5,6-dihydro-1,3-thiazine- 2-thione, m.p. 80.5°–81.5°C.

Anal. Calcd. for $C_8H_{13}NS_2$: C, 51.3; H, 7.0; N, 7.5; S, 34.2. Found: C, 51.4; H, 6.8; N, 7.3; S, 34.4.

EXAMPLE III

The analgesic properties of 4-carboxythiazolidine-2-thione were established by the acetic acid writhing test according to the method of B. A. Whittle, *Brit. J. Pharmcol.* 22, 246–253 (1964). By this test, 4-carboxythiazolidine-2-thione afforded 29% analgesia in mice at a dose level of 50 mg/kg.

EXAMPLE IV

The analgesic properties of 3,4-tetramethylene-4H,5,6-dihydro-1,3-thiazine-2-thione were established according to the above-mentioned acetic acid writhing test. The ED50, i.e., the reduction of the response in treated animals to 50 percent of the value in control animals, of the compound in mice is 13 mg/kg. The edema inhibition activity was established in the carrageenan-induced rat paw edema test according to the method of C. A. Winter, et al, *Proc. Soc. Exp. Biol. Med.*, 111, 544–547 (1962). The ED25, defined corresponding to the above, of the compound in mice is 60 mg/kg. The LD50 in mice is 315 mg/kg.

While certain embodiments of the invention have been described for illustrative purposes, the invention is not limited thereto. Various other modifications or embodiments of the invention will be apparent to those skilled in the art in view of this disclosure. Such modifications or embodiments are within the spirit and scope of the disclosure.

We claim:

1. A method for preparing 4-carboxythiazolidine-2-thione which consists of reacting an alkali metal hydroxide selected from hydroxides of sodium, potassium, rubidium, cesium, and lithium, or mixtures thereof, cysteine hydrochloride hydrate, and carbon disulfide in an aqueous reaction mixture of said reactants under reaction conditions which produce 4-carboxythiazolidine-2-thione, and recovering 4-carboxythiazolidine-2-thione from the resulting reaction mixture.

2. A method in accordance with claim 1 wherein: said alkali metal hydroxide is sodium hydroxide or potassium hydroxide.

3. A method in accordance with claim 1 wherein: the mol ratio of said alkali metal hydroxide to said hydrate is within the range of from 10 to 1; and the mol ratio of said carbon disulfide to said hydrate is within the range of from 10 to 1; and said reacting is effected at a temperature in the range 60° to 110°F.

4. A method for preparing a thiazolidine-2-thione compound which consists of reacting sodium hydroxide, cysteine hydrochloride hydrate and carbon disulfide in water at room temperature for a period of time sufficient to form said compound and recovering 4-carboxythiazolidine-2-thione thus produced.

\* \* \* \* \*